United States Patent [19]

Hussein et al.

[11] Patent Number: 4,981,929

[45] Date of Patent: Jan. 1, 1991

[54] CATALYST PRODUCTIVITY IN THE POLYMERIZATION OF OLEFINS

[75] Inventors: Fathi D. Hussein; David M. Gaines; Han T. Liu; Douglas J. Miller, all of Charleston, W. Va.

[73] Assignee: Union Carbide Chemicals and Plastics Company, Inc., Danbury, Conn.

[21] Appl. No.: 877,501

[22] Filed: Jun. 23, 1986

[51] Int. Cl.$^5$ .......................... C08F 2/34; C08F 10/00
[52] U.S. Cl. .................................. 526/125; 526/124; 526/901; 526/351
[58] Field of Search ................ 526/124, 125, 153, 901

[56] References Cited

U.S. PATENT DOCUMENTS

| | | | |
|---|---|---|---|
| 4,065,609 | 12/1977 | Willmore | 526/61 |
| 4,175,171 | 11/1979 | Ito et al. | 526/153 |
| 4,234,710 | 11/1980 | Moberly et al. | 526/906 |
| 4,302,565 | 11/1981 | Goeke et al. | 526/88 |
| 4,370,449 | 1/1983 | Bye | 526/351 |
| 4,414,132 | 11/1983 | Goodall et al. | 502/169 |
| 4,511,703 | 4/1985 | Bailly | 526/351 |
| 4,563,512 | 1/1986 | Goodall | 526/125 |

FOREIGN PATENT DOCUMENTS 132893 7/1984 European Pat. Off. .
141461 10/1984 European Pat. Off. .

*Primary Examiner*—Edward J. Smith
*Attorney, Agent, or Firm*—John S. Piscitello

[57] ABSTRACT

Highly stereospecific olefin polymers are obtained in enhanced yield in a continuous gas-phase fluid bed process for polymerizing alpha monoolefins employing a catalyst system comprising (a) a solid titanium-containing procatalyst, (b) an organoaluminum activator compound, and (c) a selectivity control agent, by continuously adding dialkylaluminum halide to the reactor during polymerization and conducting polymerization at a temperature of 0.1° to 5.0° C. above the dew point temperature of the cycle gas in the reactor.

12 Claims, 1 Drawing Sheet

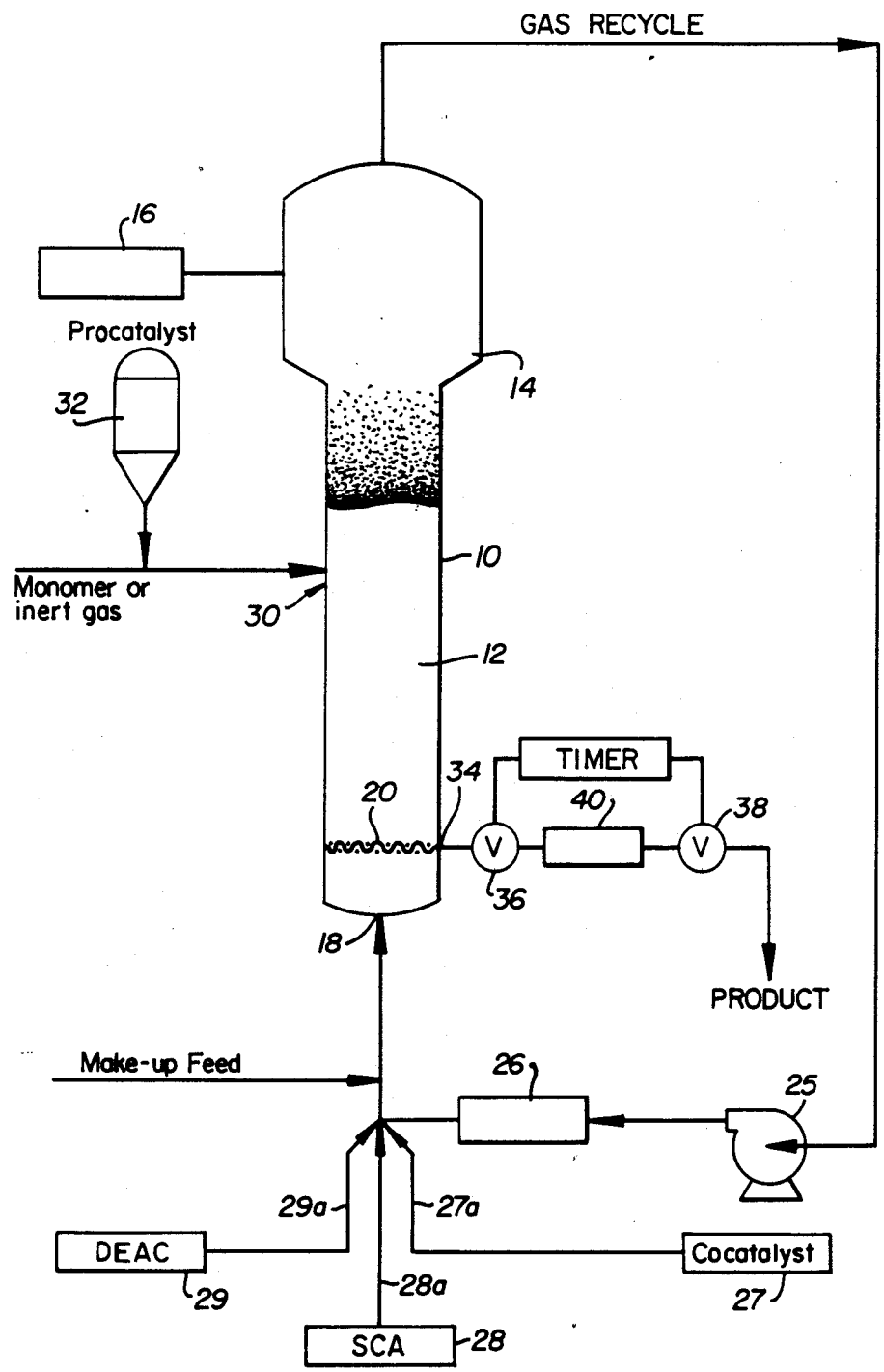

CATALYST PRODUCTIVITY IN THE POLYMERIZATION OF OLEFINS

BACKGROUND OF THE INVENTION

1. Field of the Invention

This invention relates to a process for improving the productivity of catalysts used in the continuous gas-phase, fluid bed process for the polymerization of olefins.

2. Prior Art

U.S. Pat. No. 4,414,132 to Goodall et al. teaches the use of highly active, stereospecific catalysts for the polymerization of olefins.

It is known from U.S. Pat. No. 4,065,609 to Willmore that gas phase olefin polymerization conducted in an agitated bed at from 0.1° C. to 5.0° C. of the dew point temperature of the reactants increases stereospecificity and yield of the olefin.

It is also known from European Specification No. 0141461 that productivity of the Goodall catalyst can be improved by pretreating the catalyst with dialkylaluminum chloride. However, the catalyst pretreated in this manner is so highly active that special handling techniques are required in order to introduce it into the polymerization reactor. In addition, if the catalyst is not pretreated with dialkylaluminum chloride before it is introduced into the polymerization reactor, enhanced results are not obtained according to the reference.

Independently conducted experiments have substantiated that little or no improvement is obtained when dialkylaluminum halide is added to the Goodall catalyst in the polymerization reactor under ordinary polymerization conditions. Surprisingly, however, it has now been found that an unexpected increase in catalyst activity is obtained if dialkylaluminum halide is added to the reactor near the dew point temperature of the reactants; this increase is well above that which might be expected by operating at temperatures near the dew point alone.

SUMMARY OF THE INVENTION

In accordance with the present invention, it has now been discovered that highly stereospecific olefin polymers can be obtained in enhanced yield in a continuous gas-phase fluid bed process for polymerizing alpha monoolefins employing a catalyst system comprising:
(a) a solid titanium-containing procatalyst,
(b) an organoaluminum activator compound, and
(c) a selectivity control agent, by continuously adding dialkylaluminum halide to the reactor during polymerization and conducting polymerization at a temperature 0.1° to 5.0° C. above the dew point temperature of the cycle gas in the reactor.

BRIEF DESCRIPTION OF THE DRAWINGS

The drawing shows a gas phase fluid bed reaction system which may be employed to polymerize olefins in accordance with the process of the present invention.

DETAILED DESCRIPTION OF THE INVENTION

This invention provides a process for improving the catalyst productivity in a continuous gas-phase, fluid bed process for the polymerization of olefins. More particularly, catalyst productivity is enhanced by feeding dialkylaluminum halide into the polymerization reactor in addition to procatalyst, activator compound and selectivity control agent, and by operating the reactor at a temperature slightly above the dew point of the cycle gas in the reactor. The reaction temperature and dew point temperature can be made to approach one another, i.e., within 5.0° C., by increasing the dew point temperature of the cycle gas or by lowering the temperature of the reaction. Preferably this is accomplished by raising the dew point temperature to within 5° C. of the polymerization temperature which is ordinarily conducted at a temperature of from 50° C. to 80° C., preferably from 60° C. to 70° C., and most preferably from 60° C. to 65° C.

Several methods well known in the art can be employed to elevate the dew point. These include, for example,
(a) increasing the monomer partial pressure, i.e., the partial pressure of propylene; and/or
(b) diluting the reaction mixture with an inert diluent gas.

When a diluent gas is employed to elevate the dew point of the cycle gas, it should be employed in an amount sufficient to elevate the dew point to within 0.01° to 5° C. of reaction temperature. The amount of diluent depends on the type of the diluent and can range between 1 to 30, preferably 3 to 20 mol percent of reaction mixture.

By a "diluent" gas is meant a gas which is nonreactive under the conditions employed in the polymerization reactor. i.e., does not decompose and/or react with the polymerizable monomer and the components of the catalyst composition under the polymerization conditions employed in the reactor. Among such diluents are propane, isopentane, and the like. Preferred diluent gases used for elevating the dew point are the relatively higher molecular weight inerts such as isopentane and propane. Increasing the concentrations of inerts such as nitrogen and hydrogen has little effect on the dew point of the total gaseous mixture.

The preferred method of elevating the dew point of the cycle gas, however, is by increasing the molar concentration of the reactive monomer in the reactor thus elevating the partial pressure of the gaseous mixture. The increased partial pressure has the expected effect of raising the dew point of the cycle gas.

The process of this invention can be practiced using alpha monoolefins having from 2 to 8 carbons although propylene and butylene are preferred and propylene is especially preferred. Copolymerization of alpha monoolefins is also possible using the process of the invention. Typical reactor compositions consist of 65-87% alpha monoolefin, 1-2% hydrogen and the remaining percent of other cycle gases such as nitrogen, propane and isopentane.

CATALYST PREPARATION

The catalyst compositions which can be employed in the process of this invention are disclosed in U.S. Pat. No. 4,414,132 to Goodall et al., which disclosure is hereby incorporated by reference. These compositions comprise a solid titanium-containing procatalyst in combination with an organoaluminum activator compound and a selectivity control agent.

The solid titanium-containing procatalyst is obtained by halogenating a magnesium compound of the formula $MgR_1R_2$ wherein $R_1$ is an alkoxide or aryloxide group and $R_2$ is an alkoxide or aryloxide group or halogen, with a halide of tetravalent titanium in the presence of a halohydrocarbon and an electron donor in liquid phase, and subsequently contacting the halogenated product with a tetravalent titanium compound.

Since electron donor compounds are used both in the preparation of the procatalyst and as selectivity control agents and since different electron donor compounds may be used for both these purposes in production of a given catalyst, we may refer to the electron donor compound employed in preparation of the procatalyst as "electron donor" and to the other as selectivity control agent.

Examples of halogen containing magnesium compounds that can be used as starting materials for the halogenating reaction used in preparing the procatalyst are alkoxy and aryloxy magnesium halides, such as isobutoxy magnesium chloride. ethoxy magnesium bromide, phenoxy magnesium iodide. cumyloxy magnesium bromide and naphthenoxy magnesium chloride.

Preferred magnesium compounds to be halogenated are selected from magnesium dialkoxides and magnesium diaryloxides. In such compounds the alkoxide groups suitable have from 1 to 8 carbon atoms, and preferably from 2 to 8 carbon atoms. Examples of these preferred groups of compounds are magnesium diisopropoxide, magnesium diethoxide, magnesium dibutoxide, magnesium diphenoxide, magnesium dinaphthenoxide and ethoxy magnesium isobutoxide. Magnesium diethoxide is particularly preferred.

In the halogenation with a halide of tetravalent titanium, the magnesium compounds are preferably reacted to form a magnesium halide in which the atomic ratio of halogen to magnesium is at least 1:2. Better results are obtained when the halogenation proceeds more completely, i.e., yielding magnesium halides in which the atomic ratio of halogen to magnesium is at least 1.5:1. The most preferred reactions are those leading to fully halogenated reaction products, i.e., magnesium dihalides. Such halogenation reactions are suitably effected by employing a molar ratio of magnesium compound to titanium compound of 0.005:1 to 2.0:1, preferably 0.01:1 to 1:1. These halogenation reactions are conducted in the additional presence of an halohydrocarbon and an electron donor. An inert hydrocarbon diluent or solvent may also be present. When using an inert diluent or solvent, this should of course not be used as a complete substitute for the halohydrocarbon, for it is essential that the halogenation reaction proceeds in the presence of a halohydrocarbon.

Suitable halides of tetravalent titanium include aryloxy- or alkoxy-di- and -trihalides, such as dihexanoxy-titanium dichloride, diethoxy-titanium dibromide, isopropoxy-titanium tri-iodide and phenoxy-titanium trichloride; titanium tetrahalides are preferred; most preferred is titanium tetrachloride.

Suitable halohydrocarbons include compounds containing a single halogen atom per molecule, such as butyl chloride, amyl chloride, as well as compounds containing more than one halogen atom per molecule. Preferred aliphatic halohydrocarbons are halogen-substituted hydrocarbons with 1 to 12, particularly less than 9, carbon atoms per molecule, and at least two halogen atoms, such as dibromomethane, trichloromethane, 1,2-dichloroethane, dichlorobutane, 1,1,2-trichloroethane, trichlorocyclohexane, dichlorofluoroethane, trichloropropane, trichlorofluoroctane, dibromodifluorodecane, hexachloroethane and tetrachloroisooctane. Carbon tetrachloride and 1,1,2-trichloroethane are preferred aliphatic halohydrocarbons. Aromatic halohydrocarbons may also be employed, e.g., chlorobenzene, bromobenzene, dichlorobenzene, dichlorodibromobenzene, naphthyl chloride, chlorotoluene, dichlorotoluenes, and the like; chlorobenzene and dichlorobenzene are preferred aromatic halohydrocarbons.

The halogenation normally proceeds until formation of a solid reaction product which may be isolated from the liquid reaction medium by filtration, decantation or another suitable method and subsequently washed with an inert hydrocarbon diluent, such as n-hexane, isooctane or toluene, to remove any unreacted material, including physically absorbed halohydrocarbon.

Subsequent to halogenation, the product is contacted with a tetravalent titanium halide such as a dialkoxy-titanium dihalide, alkoxy-titanium trihalide, phenoxy-titanium trihalide or titanium tetrahalide a second time. The most preferred titanium compounds are titanium tetrahalides and especially titanium tetrachloride. This treatment increases the content of tetravalent titanium in the solid catalyst component. This increase should preferably be sufficient to achieve a final atomic ratio of tetravalent titanium to magnesium in the solid catalyst component of from 0.005 to 3.0, particularly of from 0.02 to 1.0. To this purpose the contacting with the tetravalent titanium chloride is most suitably carried out at a temperature of from 60° to 136° C. during 0.1–6 hours, optionally in the presence of an inert hydrocarbon diluent. Particularly preferred contacting temperatures are from 70° to 120° C. and the most preferred contacting periods are in between 0.5 to 3.5 hours. The treatment may be carried out in successive contacts of the solid with separate portions of $TiCl_4$.

After the treatment with tetravalent titanium chloride the procatalyst is suitably isolated from the liquid reaction medium and washed to remove unreacted titanium compound. The titanium content of the final, washed procatalyst is suitably between about 1.5 to 3.6 percent by weight or up to about 4.5 percent.

The preferred halogen atom, possibly contained in the magnesium compound to be halogenated, and contained in the titanium compound which serves as halogenating agent and in the tetravalent titanium halide with which the halogenated product is contacted, is chlorine.

Suitable compounds which may serve as electron donors in the preparation of the procatalyst are ethers, esters, ketones, phenols, amines, amides, imines, nitriles, phosphines. phosphites, stibines, arsines, phosphoramides and alcoholates. Examples of suitable compounds are those referred to in U.S. Pat. No. 4,136,243 or its equivalent British Specification No. 1,486,194 and in British Specification No. 1,554,340 or its equivalent German Offenlegungsschrift No. 2,729,126. Preferred compounds are esters and diamines, particularly esters of aromatic carboxylic acids, such as ethyl and methyl benzoate, p-methoxy ethyl benzoate, p-ethoxy methyl benzoate, ethyl acrylate, methyl methacrylate, ethyl acetate, dimethyl carbonate, dimethyl adipate, dihexyl fumarate, dibutyl maleate, ethylisopropyl oxalate, p-chloro ethyl benzoate, p-amino hexyl benzoate, isopropyl naphthenate, n-amyl toluate, ethyl cyclohexanoate, propyl pivalate, N,N,N',N',-tetramethylethylene diamine, 1,2,4-trimethyl piperazine, 2,3,4,5-tetraethyl-piperidine and similar compounds. The preferred electron donors for use in preparing the procatalyst are ethyl benzoate and p-methyl toluate.

Proportions of electron donor contained in the formation of procatalyst, calculated as mol per mol of magnesium, are suitably in the range of from 0.01 to 10, e.g. from 0.05 to 10, preferably from 0.1 to 5.0 and more preferably from 0.01 to 1.0.

The compound used as selectivity control agent may be the same as or different from the electron donor compound used for preparing the procatalyst. The preferred selectivity control agents are p-ethyl anisate or ethyl p-ethoxy benzoate.

The organoaluminum compound to be employed as activator is most suitably a trialkylaluminum compound of the formula $R_3Al$, wherein R has 2 to 6 carbon atoms, e.g., triethylaluminum, tri-n-propylaluminum, triisobutylaluminum, triisopropylaluminum and dibutyl-n-amylaluminum.

In a preferred mode, the procatalyst of the process is a $MgCl_2$ supported $TiCl_4$ solid catalyst containing an inside electron donor such as ethylbenzoate, the activator is triethylaluminum and the selectivity control agent is para-ethylethoxybenzoate.

The dialkylaluminum halide which is added to the reaction system in addition to the procatalyst, trialkylaluminum activator and selectivity control agent can be represented by the formula $R_2AlX$ wherein R is an alkyl radical containing from 1 to 8 carbon atoms and X is halogen, preferably chlorine. The preferred dialkylaluminum halide is diethylaluminum chloride.

THE POLYMERIZATION REACTION

The polymerization reaction is conducted by continuously contacting a stream of one or more olefin monomers, e.g., propylene, in a gas phase and substantially in the absence of catalyst poisons such as moisture, oxygen, carbon monoxide, carbon dioxide and acetylene with a catalytically effective amount of the catalyst composition described above while continually adding dialkylaluminum halide to the reactor during polymerization and conducting polymerization at a temperature 0.1° to 5.0° C. above the dew point of the cycle gas in the reactor.

A fluidized bed reaction system which can be used in the practice of the process of the present invention is illustrated in the accompanying drawing. With reference thereto the reactor 10 consists of a reaction zone 12 and a velocity reduction zone 14.

The reaction zone 12 comprises a bed of growing polymer particles, formed polymer particles and a minor amount of catalyst particles fluidized by the continuous flow of polymerizable and modifying gaseous components in the form of make-up feed and a recycle gas through the reaction zone. To maintain a viable fluidized bed, the superficial gas velocity through the bed must exceed the minimum flow required for fluidization, and preferably is at least 0.2 feet per second above the minimum flow. Ordinarily the superficial gas velocity does not exceed 5.0 feet per second and most usually no more than 2.5 feet per second is sufficient.

It is essential that the bed always contains particles to entrap and distribute the particulate catalyst throughout the reaction zone. On start up, the reaction zone is usually charged with a base of particulate polymer particles before gas flow is initiated. Such particles may be identical in nature to the polymer to be formed or different therefrom. Eventually, a fluidized bed of the desired polymer particles supplants the start-up bed.

Fluidization is achieved by a high rate of gas recycle to and through the bed, typically in the order of about 50 times the rate of feed of make-up gas. The fluidized bed has the general appearance of a dense mass of viable particles in possible free-vortex flow as created by the percolation of gas through the bed. The pressure drop through the bed is equal to or slightly greater than the mass of the bed divided by the cross-sectional area. It is thus dependent on the geometry of the reactor.

Make-up gas, which generally consists of the monomer, nitrogen and hydrogen, but may also contain isopentane, propane, or other diluent gas, is fed to the bed at a rate to keep a steady state gaseous composition. The composition of the make-up gas is determined by a gas analyzer 16 positioned above the bed. The gas analyzer determines the composition of the gas being recycled and the composition of the make up gas is adjusted accordingly to maintain an essentially steady state gaseous composition within the reaction zone.

To insure complete fluidization the recycle gas and, where desired, part of the make-up gas are returned to the reactor at point 18 below the bed. There exists a gas distribution plate 20 above the point of return to aid fluidizing the bed.

The portion of the gas stream which does not react in the bed constitutes the recycle gas which is removed from the polymerization zone, preferably by passing it into a velocity reduction zone 14 above the bed where entrained particles are given an opportunity to drop back into the bed. The recycle gas is then compressed in a compressor 25 and then passed through a heat exchanger 26 wherein it is stripped of heat of reaction before it is returned to the bed. By constantly removing heat of reaction, no noticeable temperature gradient appears to exist within the upper portion of the bed and the temperature of the reaction is maintained constant. A temperature gradient will exist in the bottom of the bed in a layer of about 6 to 12 inches, between the temperature of the inlet gas and the temperature of the remainder of the bed. Thus, it has been observed that the bed acts to almost immediately adjust the temperature of the recycle gas above this bottom layer of the bed zone to make it conform to the temperature of the remainder of the bed thereby maintaining itself at an essentially constant temperature under steady conditions. The recycle is then returned to the reactor at its base 18 and to the fluidized bed through distribution plate 20. The compressor 25 can also be placed downstream of the heat exchanger 26.

The distribution plate 20 plays an important role in the operation of the reactor. The fluidized bed contains growing and formed particulate polymer particles as well as catalyst particles. Diffusing recycle gas through the bed at a rate sufficient to maintain fluidization at the base of the bed is, therefore, important. The distribution plate 20 serves this purpose and may be a screen, slotted plate, perforated plate, a plate of the bubble cap type and the like. The elements of the plate may all be stationary, or the plate may be of the mobile type disclosed in U.S. Pat. No. 3,298,793. Whatever its design, it must diffuse the recycle gas though the particles at the base of the bed to keep them in a fluidized condition, and also serve to support a quiescent bed of resin particles when the reactor is not in operation.

REACTANTS

The procatalyst used in the fluidized bed is preferably stored for service in a reservoir 32 under a blanket of gas which is inert to the stored material, such as nitrogen or argon, and can be conveyed to the bed by means of a monomer or an inert.

The procatalyst is conveniently and preferably fed to the reactor dissolved in or diluted with an inert liquid solvent, i.e., a solvent which is nonreactive with all the components of the procatalyst composition and all the other active components of the reaction system. Hydrocarbons such as isopentane, hexane, heptane, toluene, xylene, naphtha and mineral oil are preferred for this purpose. Generally, the procatalyst suspension or solution employed contains from 0.1 weight percent to 75 weight percent of the procatalyst, usually from 5 weight percent to 40 weight percent of the procatalyst. If desired, less concentrated or more concentrated suspensions or solutions can be employed, or, alternatively, the procatalyst can be added in the absence of solvent.

Any solvent employed to introduce the procatalyst into the reactor is, of course, immediately either vaporized in the reactor and becomes part of the inert gaseous portion of the cycle gas or it stays in the polyolefin particles. The amount of solvent should, of course, be carefully controlled to minimize the residuals in the polyolefin product.

The procatalyst is injected into the bed at a rate equal to its consumption at a point 30 which is above the distribution plate 20.

The organoaluminum activator compound, e.g., triethylaluminum, can also be added directly to the bed but is preferably added to the gas recycle system. Addition to the recycle line downstream from the heat exchanger is preferred, as from dispenser 27 thru line 27A. In general, enough activator should be added such that the atomic ratio aluminum in the activator to titanium in the procatalyst, Al:Ti, is in the range of 40:1 to 100:1, more preferably in the range of 50:1 to 80:1.

The organoaluminum activator, like the procatalyst, can be fed to the reactor either dissolved in or diluted with an inert liquid solvent, or alternatively it may be added in the absence of solvent. The same inert solvents which can be employed to convey the procatalyst may be employed to convey the activator. Generally, the suspension or solution of activator contains from 5 weight percent to 75 weight percent of the activator. The feed rate of the activator is based on the procatalyst feed rate and, as noted above, such that the molar ratio of aluminum to titanium is greater than 40. Further, the ratio of activator to selectivity control agent helps determines the isotacticity of the polyolefin product.

The selectivity control agent, e.g. ethyl p-ethoxy benzoate or p-ethyl anisate, can also be added directly to the bed but is preferably added to the gas recycle system. Addition to the recycle line downstream from the heat exchanger is preferred, as from dispenser 28 thru line 28A. Preferred proportions of selectivity control agent (SCA). calculated as mol per mol aluminum activator compound, are in the range from 0.1 to 1.0 particularly from 0.2 to 0.5.

The selectivity control agent, like the procatalyst or activator, can be fed to the reactor either dissolved in or diluted with an inert liquid solvent, or alternatively, it may be added in the absence of solvent The same inert solvents which can be employed to convey the procatalyst and activator may be employed to convey the selectivity control agent. Generally, the suspension or solution of selectivity control agent contains from 5 weight percent to 75 weight percent of the selectivity control agent.

The dialkylaluminum halide can also be added directly to the fluid bed but is preferably added to the gas recycle system. Addition to the recycle line downstream from the heat exchanger is preferred, as from dispenser 29 thru line 29A. The dialkylaluminum halide is added at a controlled flow based on the procatalyst feed rate such that the molar ratio of dialkylaluminum halide to titanium is 5 to 25:1, preferably 10–20:1.

The dialkylaluminum halide, like the procatalyst, activator or selectivity control agent, can be fed to the reactor either dissolved in or diluted with an inert liquid solvent, or alternatively, it may be added in the absence of solvent. The same inert solvents which can be employed to the other reactants may be employed to convey the dialkylaluminum halide. Generally, the suspension or solution of dialkylaluminum halide contains from 5 weight percent to 75 weight percent of the dialkylaluminum halide.

Hydrogen which may be added as part of the makeup feed gas through line 18 is used as a chain transfer agent in the polymerization reaction of the present invention to control the molecular weight of the polymer without detriment to the stereospecific performance of the catalyst compositions. The ratio of hydrogen/monomer employed will vary between about 0 to about 0.7 moles, preferably 0 to 0.3, of hydrogen per mole of the monomer in the gas stream.

Other gases inert to the catalyst composition, e.g. Propane, nitrogen, can also be added to the gas stream through line 18.

The polymer production rate of the bed is controlled by the rate of injection of the catalyst components. The productivity of the bed may be increased by simply increasing the rate of injection of the components and decreased by reducing the rate of injection.

Since any change in the rate of injection of the catalyst components will change the rate of generation of the heat of reaction, the temperature of the recycle gas is adjusted upwards or downwards to accommodate the change in rate of heat generation. This insures the maintenance of an essentially constant temperature in the bed. Complete instrumentation of both the fluidized bed and the recycle gas cooling system, is, of course, necessary to detect any temperature change in the bed so as to enable the operator to make a suitable adjustment in the temperature of the recycle gas Under a given set of operating conditions, the fluidized bed is maintained at essentially a constant height by withdrawing a portion of the bed as product at a rate equal to the rate of formation of the particulate polymer product. Since the rate of heat generation is directly related to product formation, a measurement of the temperature rise of the gas across the reactor (the difference between inlet gas temperature and exist gas temperature) is determinative of the rate of particulate polymer formation at a constant gas velocity.

The particulate polymer product is preferably continuously withdrawn at a point 34 at or close to the distribution plate 20 and in suspension with a portion of the gas stream which is vented before the particles settle. The suspending gas may also be used as mentioned above, to drive the product of one reactor to another reactor.

It should be noted that the activity and stereospecificity of the catalyst compositions leaves no need for any catalyst removal or polymer extraction techniques. Total residues in the polymer, i.e., the combined aluminum, chlorine and titanium content, can be as low as 200 ppm. even less than 100 ppm.

The particulate polymer product is conveniently and preferably withdrawn through the sequential operation of a pair of timed valves 36 and 38 defining a segregation zone 40. While valve 38 is closed, valve 36 is opened to emit a plug of gas and product to the zone 40 between it and valve 36 which is then closed. Valve 38 is then opened to deliver the product to an external recovery zone. Valve 38 is then closed to await the next product recovery operation.

The fluidized bed reactor is equipped with an adequate venting system to allow venting the bed during start up and shut down. The reactor does not require the use of stirring means and/or wall scraping means.

The fluid bed reactor is operated at pressures of up to about 1000 psi, and is preferably operated at a pressure of from about 150 to 600 psi, and more preferably from 400 to 600 psi.

EXAMPLES

The following examples and procedures are presented to illustrate the invention, but are not to be construed as limiting thereon. Those examples considered to illustrate the invention are numbered and comparative examples are lettered.

| | Definitions |
|---|---|
| g | grams |
| mg | milligrams |
| wt. % | weight percent |
| % | percent |
| $H_2$ | hydrogen |
| ml | milliliters |
| mol | moles |
| mmol | millimoles |
| MFi | melt flow index |
| DEAC | diethylaluminumchloride |
| Ti | titanium |
| $T_{Reaction}$ | reaction temperature |
| $T_{DP}$ | dew point temperature |
| PSIA | pounds per square inch [Absolute] |
| XS | xylene solubles - measure of isotacticity |

EXAMPLE 1

Preparation of Procatalyst 10 grams of magnesium turnings (412 mat) were reacted at room temperature with ethanol employing a mixture comprising 100 ml ethanol, 20 ml xylene, 5 mg of mercuric chloride (0.02 mmol) and 3 mg of iodine (0.02 mmol) The reaction took 5 hours for completion. Subsequently, the liquid phase was removed by distillation and the resulting solid was dried under a nitrogen vacuum.

10 mmol of the magnesium di-ethoxide so prepared was suspended in 15 ml chlorobenzene and at 75° C.-85° C. 0.48 ml ethyl benzoate (3.3 mmol) and 15 ml of titanium tetrachloride (136 mmol) were added. The suspension was stirred at that temperature for 1-2 hours. The solid formed was isolated from the reaction medium by filtering and decantation (component a).

This component a was reacted in a mixture of 15 ml titanium tetrachloride (136 mmol) and 15 ml chlorobenzene again et 75° C.-85° C. and the suspension was stirred at that temperature for 2 hours. The solid was filtered and decanted (component b).

Component b was again reacted in a mixture of 15 ml titanium tetrachloride and 15 ml chlorobenzene and benzoyl chloride (0.02 ml) was mixed in. The mixture was heated once more to 75° C.-85° C. for 1 to 2 hours, filtered and drained. The solid was then washed five times in isooctane and the procatalyst was placed in mineral oil.

General Procedures

Propylene was homopolymerized under varying reaction conditions in a fluid bed reactor system similar to the one described and illustrated herein.

In each polymerization, procatalyst composition prepared in accordance with Example 1 and diluted with mineral oil to form a 40% solution was continually fed to the polymerization reactor along with triethylaluminum, as a solution in isopentane [or undiluted], diethylaluminum chloride, also as a solution in isopentane [or undiluted], and ethyl p-ethoxy benzoate, also as a solution in isopentane [or undiluted].

The propylene gas employed, in each instance, was added to the reaction mixture. Nitrogen and other inerts, if needed, were also added to the reaction mixture. Hydrogen was added to the reaction mixture as a chain transfer agent to regulate the molecular weight of the copolymer produced.

EXAMPLES 2-5

Examples 2 through 5 in Tables I through IV below are examples of when both parameters of the invention were met, i.e., the reaction temperature was 5° C. or less above the dew point temperature of the cycle gas and diethylaluminum chloride [DEAC] was added to the reactor in addition to procatalyst, organoaluminum activator and selectivity control agent. In each instance, productivity increases of 40 to 65% were realized compared to Examples showing no DEAC addition and temperatures well above dew point (Comparative Examples A and C) or compared to Examples showing DEAC addition but with temperature still away from dew point (Comparative Examples D and F). Significant improvements in productivity were displayed over examples close to dew point but where no DEAC was added (Comparative Examples B, E and G).

Specifically, examples from Tables I and II were conducted at lower pressure and inert diluents were used to elevate cycle gas dew point while no inert diluents were used to elevate dew point in the examples from Tables III and IV. It should be noted that in both cases, examples where both parameters of the invention were met resulted in productivity gains much more significant than would be expected by operating near dew point alone.

It should also be noted that a greater percentage of xylene solubles, as in Table IV versus Table III results in greater productivity gains.

Various reaction conditions are given for each example.

TABLE I

| Example | Comparative A | Comparative B | 2 |
|---|---|---|---|
| MF g/10 min | 3.3 | 1.0 | 3.6 |
| xylene solubles % | 3.0 | 2.9 | 3.0 |
| Productivity* Kg Polymer/g Ti | 197 | 254 | 321 |
| Percent improvement in productivity of catalyst | — | 29% | 63% |
| Reactor Pressure (PSIA) | 415 | 440 | 415 |
| Temperature of Reaction (°C.) | 65° C. | 65° C. | 65° C. |
| Dew Point of Cycle Gas (°C.) | under 55° C. | 61° C. | 62.7° C. |

TABLE I-continued

| Example | Comparative A | Comparative B | 2 |
|---|---|---|---|
| Operation close to D.P. ($T_{reaction}-T_{DP}$)°C. | No; >10° C. | Yes; 4° C. | Yes; 2.3° C. |
| DEAC Added (DEAC/Ti) Molar | No | No | Yes; 17:1 |
| Aluminum in Activator: Ti in procatalyst | 36:1 | 130:1 | 61:1 |
| Al:SCA | 2.3:1 | 2.4:1 | 2.0:1 |
| Mol % propylene | 72% | 77% | 71.5% |
| Mol % isopentane | .2% | .4% | 4.3% |
| Mol % inert propane | — | 13% | — |

*Productivity is corrected to the same propylene partial pressure of 330 PSIA

TABLE II

| Example | Comparative C | 3 |
|---|---|---|
| MF g/10 min | 3.6 | 4.0 |
| xylene solubles % | 3.8 | 3.6 |
| Productivity* Kg Polymer/g Ti | 294 | 461 |
| Percent Improvement in productivity of catalyst | — | 56% |
| Reactor Pressure (PSIA) | 440 | 440 |
| Temperature of Reaction (°C.) | 62° C. | 60° C. |
| Dew Point of Cycle (°C.) | under 52° C. | 56° C. |
| Operation close to D.P. ($T_{reaction}-T_{DP}$)°C. | No; >10° C. | Yes; 4° C. |
| DEAC Added (DEAC/Ti) Molar | No | Yes; 26:1 |
| Aluminum in Activator: Ti in procatalyst | 69:1 | 131:1 |
| Al:SCA | 1.8:1 | 1.7:1 |
| Mol % propylene | 74.5% | 63.8% |
| Mol % isopentane | .5% | .9% |
| Mol % inert propane | — | 16% |

*Productivity is corrected to the same propylene partial pressure of 330 PSIA

TABLE III

| Example | Comparative D | Comparative E | 4 |
|---|---|---|---|
| MF g/10 min | 7.9 | 1.8 | 1.4 |
| xylene solubles % | 3.4 | 3.4 | 3.3 |
| Productivity* Kg Polymer/g Ti | 371 | 460 | 528 |
| Percent improvement in productivity of catalyst | — | 24% | 42% |
| Reactor Pressure (PSIA) | 490–500 | 490–500 | 490–500 |
| Temperature of Reaction (°C.) | 62°–64° C. | 65° C. | 65° C. |
| Dew Point of Cycle Gas (°C.) | under 52° C. | 63.4° C. | 64° C. |
| Operation close to D.P. ($T_{reaction}-T_{DP}$)°C. | No; >10° C. | Yes; 1.6° C. | Yes; 1° C. |
| DEAC Added (DEAC/Ti) Molar | Yes; 10:1 | No | Yes; 10:1 |
| Aluminum in Activator: Ti in procatalyst | 40:1 | 32:1 | 41:1 |
| Al:SCA | 1.9:1 | 3.4:1 | 2.2:1 |
| Mol % propylene | 73% | 82% | 85% |
| Mol % isopentane | — | — | — |
| Mol % inert propane | — | — | — |

*Productivity is corrected to the same propylene partial pressure of 330 PSIA

TABLE IV

| Example | Comparative F | Comparative G | 5 |
|---|---|---|---|
| MF g/10 min | 8.0 | 1.6 | 1.4 |
| xylene solubles % | 3.8 | 3.8 | 3.7 |
| Productivity* Kg Polymer/g Ti | 402 | 546 | 610 |
| Percent improvement in productivity of catalyst | — | 36% | 52% |
| Reactor Pressure (PSIA) | 490–500 | 490–500 | 490–500 |
| Temperature of Reaction (°C.) | 64° C. | 65° C. | 65° C. |
| Dew Point of Cycle Gas (°C.) | under 54° C. | 63.6° C. | 62.6° C. |
| Operation close to D.P. ($T_{reaction}-T_{DP}$)°C. | No; >10° C. | Yes; 1.9° C. | Yes; 2.4° C. |
| DEAC Added (DEAC/Ti) Molar | Yes; 10:1 | No | Yes; 10:1 |
| Aluminum in Activator: Ti in procatalyst | 40:1 | 34.5:1 | 37.9:1 |
| Al:SCA | 1.8:1 | 3.2:1 | 2.6:1 |
| Mol % propylene | 75.6% | 82.0% | 84.0% |
| Mol % isopentane | — | — | — |
| Mol % inert propane | — | — | — |

*Productivity is corrected to the same propylene partial pressure of 330 PSIA

We claim:

1. In a process for polymerizing alpha monoolefins in a continuous gas-phase fluid bed process employing a catalyst system comprising (a) a solid titanium-containing procatalyst, said solid titanium-containing procatalyst having been obtained by halogenating a magnesium compound of the formula $MgR_1R_2$ wherein $R_1$ is an alkoxide or aryloxide group and $R_2$ is an alkoxide or aryloxide group or halogen, with a halide of tetravalent titanium in the presence of a halohydrocarbon and an electron donor in liquid phase, and subsequently contacting the halogenated product with a tetravalent titanium halide, and washing it to remove unreacted titanium compounds and recover the solid product, (b) an organoaluminum activator compound and (c) a selectivity control agent, the improvement which comprises continually adding dialkylaluminum halide to the reactor during polymerization and conducting polymerization at a temperature of 0.1° to 5.0° C. above the dew point of the cycle gas in the reactor.

2. A process as in claim 1 wherein the solid titanium-containing procatalyst is a $MgCl_2$ supported $TiCl_4$ solid catalyst containing an electron donor.

3. A process as in claim 2 wherein the electron donor is ethyl benzoate.

4. A process as in claim 1 wherein the organoaluminum activator is a trialkylaluminum compound of the formula $R_3Al$ wherein R has 2 to 6 carbons.

5. A process as in claim 4 wherein $R_3Al$ is triethylaluminum.

6. A process as in claim 1 wherein the selectivity control agent is ethyl p-ethoxy benzoate.

7. A process as in claim 1 wherein the selectivity control agent is p-ethyl anisate.

8. A process as in claim 1 wherein the dialkylaluminum halide is $R_2AlX$ wherein R is an alkyl group having 1 to 8 carbons and X is a halogen.

9. A process as in claim 8 wherein $R_2AlX$ is diethylaluminum chloride.

10. A process as in claim 1 wherein the solid titanium-containing procatalyst is a $MgCl_2$ supported $TiCl_4$ solid catalyst, the organoaluminum activator is triethylaluminum, the selectivity control agent is ethyl p-ethoxy benzoate and the dialkylaluminum halide is diethylaluminum chloride.

11. A process as in claim 1 wherein the ratio of activator to titanium is 40:1 to 100:1.

12. A process as in claim 1 wherein the ratio of dialkylaluminum halide to titanium is 5:1 to 25:1.

* * * * *